US012590303B2

(12) United States Patent
Emery

(10) Patent No.: US 12,590,303 B2
(45) Date of Patent: Mar. 31, 2026

(54) SCREENING OF FLUORESCENT MICROBES USING MICROFABRICATED DEVICE

(71) Applicant: General Automation Lab Technologies Inc., San Carlos, CA (US)

(72) Inventor: Crystal Emery, San Carlos, CA (US)

(73) Assignee: ISOLATION BIO INC., San Carlos, CA (US)

( * ) Notice: Subject to any disclaimer, the term of this patent is extended or adjusted under 35 U.S.C. 154(b) by 902 days.

(21) Appl. No.: 17/555,095

(22) Filed: Dec. 17, 2021

(65) Prior Publication Data

US 2022/0193666 A1     Jun. 23, 2022

Related U.S. Application Data

(60) Provisional application No. 63/126,999, filed on Dec. 17, 2020.

(51) Int. Cl.

| | |
|---|---|
| *C12N 15/10* | (2006.01) |
| *C12Q 1/10* | (2006.01) |
| *G01N 21/64* | (2006.01) |
| *G06T 7/00* | (2017.01) |
| *C12R 1/19* | (2006.01) |

(52) U.S. Cl.
CPC ........... *C12N 15/1086* (2013.01); *C12Q 1/10* (2013.01); *G01N 21/6452* (2013.01); *G01N 21/6486* (2013.01); *G06T 7/0002* (2013.01); *C12R 2001/19* (2021.05)

(58) Field of Classification Search
CPC .................................................. G01N 21/6486
See application file for complete search history.

(56) References Cited

U.S. PATENT DOCUMENTS

| | | |
|---|---|---|
| 2017/0074872 A1 | 3/2017 | DeLouise et al. |
| 2018/0051310 A1* | 2/2018 | Hallock .................. C12Q 1/04 |
| 2018/0291418 A1 | 10/2018 | Tipgunlakant et al. |
| 2019/0200923 A1 | 7/2019 | Patolsky et al. |
| 2019/0374945 A1 | 12/2019 | Hallock |

FOREIGN PATENT DOCUMENTS

| | | |
|---|---|---|
| WO | 20218005391 A1 | 1/2018 |
| WO | 2020185817 A1 | 9/2020 |

OTHER PUBLICATIONS

J. L. Kolanowski et al., Fluorescent Probes for the Simultaneous Detection of Multiple Analytes in Biology, 47 Chem. Soc. Rev. 195-208 (2018).*
X. Xin and S.-T. Yang, Development of a Dual Fluorescence System for Simultaneous Detection of Two Cell Populations in a 3D Coculture, 86 Process Biochem. 144-150 (2019).*
G. Yin et al., A Novel Fluorescent Probe with Dual-Sites for Simultaneously Monitoring Metabolisms of Cysteine in Living Cells and Zebrafishes, 241 Spectrochimica Acta Part A 118602-1-118602-8 (2020).*
R. B. Keithley et al., Capillary Electrophoresis With Three-Color Fluorescence Detection for the Analysis of Glycosphingolipid Metabolism, 138 Analyst 164-170 (2013).*
Q. Li et al., Multicolor Fluorescence Detection-Based Microfluidic Device for Single-Cell Metabolomics: Simultaneous Quatitation of Multiple Small Molecules in Primary Liver Cells, 88 Anal. Chem. 8610-8616 (2016).*
S. A. Mojica et al., Red Fluorescent Chlamydia Trachomatis Applied to Live Cell Imaging and Screening for Antibacterial Agents, 9 Front. Microbiol. 1-13 (2018).*
International Search Report and Written Opinion on PCT/US2021/064101, mailed on Feb. 28, 2022.
Supplementary European Search Report on EP21907917, mailed on Sep. 23, 2024.
First Examination Report of Indian application on 202247022824, mailed on Mar. 7, 2025.
Chen, J.L. et al. Biotech. Bioeng. Vo. 115, No. 2, 351-358, 2018.
Xu, W. et al. Anal. Chem. vol. 82, No. 8, p. 3161-3167, 2010.
Office action notice from JPO on JP 2023-536869.

* cited by examiner

*Primary Examiner* — Randy Boyer
(74) *Attorney, Agent, or Firm* — Yong Chen; Lin Sun-Hoffman; Liu Chen & Hoffman LLP

(57) ABSTRACT

A method of identifying a fluorescent cell in a sample using a microfabricated chip having a top surface including a plurality of microwells. At least one cell of a sample is loaded into at least one microwell of the plurality of microwells. The microfabricated chip is incubated to grow a population of cells from the at least one cell in the at least one microwell. Fluorescence exhibited by at least one microwell is detected by analyzing an image of the microfabricated chip, to thereby determine a presence of a fluorescent cell of interest in the sample.

6 Claims, 5 Drawing Sheets

312 — Sealing tape

310

308 — Polycarbonate cover with fill holes

306 — gasket

304 — membrane

302 — Chip with soil microbes in wells

300

SCREENING OF FLUORESCENT MICROBES USING MICROFABRICATED DEVICE

BACKGROUND

Bacteria are small single cell organisms that are omni-present, and millions of bacteria exist in the in human body. While most bacteria are harmless to humans, some bacteria can cause serious health problems. Multidrug-resistant pathogenic bacteria are becoming a serious issue worldwide due to the wide use of antibiotics. The identification of bacterial strains or species in the human microbiome can be critical for the treatment of bacterial infections and the development of antibiotics.

Various techniques have been used for bacterial detection, such as polymerase chain reaction (PCR), gram-staining, immunological techniques, and Raman spectroscopy. However, these methods are often time-consuming, expensive, require complex procedures, and can lead to false positive results.

Fluorescence-based dyes, which are small organic probes, may be used to discriminate bacteria. Some bacterial may naturally produce fluorescence. While detection of fluorescent bacteria can be accomplished using various methods, to separate fluorescent from non-fluorescent bacteria for cultivation on a large scale, fluorescence-activated cell sorting (FACS) is typically used. A FACS instrument identifies single fluorescent bacterial cells using lasers as the excitation source and a suite of wavelength detectors to detect emissions. Then, it uses electromagnets to sort them.

SUMMARY OF THE INVENTION

In one aspect, a method of identifying a fluorescent cell in a sample is provided. The method utilizes a microfabricated chip having a top surface including a plurality of microwells. The method includes: loading at least one cell of a sample into at least one microwell of the plurality of microwells; incubating the microfabricated chip to grow a population of cells from the at least one cell in the at least one microwell; and detecting fluorescence exhibited by at least one microwell by analyzing an image of the microfabricated chip, to thereby determine a presence of a fluorescent cell of interest in the sample.

In some embodiments, the loading includes loading a plurality of cells of the sample into the plurality of microwells such that at least some of the plurality of microwells each contain one and only one cell, while none or only statistically insignificant percentage of the plurality of microwells contains more than one cell.

In some embodiments, the at least one microwell of the plurality of microwells is also loaded with a metabolic indicator indicating cell metabolic activity. The indicator can be fluorescent, and the fluorescence status of which can indicate cell metabolic activity, e.g., cell growth and proliferation. In some of such embodiments, the detecting comprises detecting fluorescence of the metabolic indicator and fluorescence of the population of cells simultaneously at separate fluorescence detection channels.

In some embodiments, if fluorescence of the population of cells is detected, at least one cell from the population of cells in the at least one microwell can be transferred to a target location.

In some embodiments, a membrane can be applied on the microfabricated device to retain the at least one cell loaded in the at least one microwell.

In another aspect, a method of identifying a fluorescent cell in a sample is provide. The method utilizes a microfabricated chip having a top surface including a plurality of microwells, and includes: (a) loading at least one cell of a sample and a fluorescent metabolic indicator into at least one microwell of the plurality of microwells, the fluorescence status of the metabolic indicator indicating presence or absence of cell metabolic activity (such as growth and proliferation); (b) incubating the microfabricated chip to grow a population of cells from the at least one cell in the at least one microwell; and (c) detecting fluorescence exhibited by at least one microwell by analyzing an image of the microfabricated chip, to thereby determine a presence of a fluorescent cell of interest in the sample. In some embodiments, detecting fluorescence exhibited by at least one microwell comprises detecting fluorescence of the metabolic indicator and fluorescence of the population of cells simultaneously at separate fluorescence detection channels.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION OF EMBODIMENTS OF THE INVENTION

An object of the present invention is to provide a method for identifying fluorescent microbes using a high-density cell cultivation and screening platform.

In some embodiments, the high density cell cultivation platform can be a microfabricated device (or a "microfabricated chip"). As used herein, a microfabricated device or chip may define a high density array of microwells (or experimental units). For example, a microfabricated chip comprising a "high density" of microwells may include about 150 microwells per $cm^2$ to about 160,000 microwells or more per $cm^2$ (for example, at least 150 microwells per $cm^2$, at least 250 microwells per $cm^2$, at least 400 microwells per $cm^2$, at least 500 microwells per $cm^2$, at least 750 microwells per $cm^2$, at least 1,000 microwells per $cm^2$, at least 2,500 microwells per $cm^2$, at least 5,000 microwells per $cm^2$, at least 7,500 microwells per $cm^2$, at least 10,000 microwells per $cm^2$, at least 50,000 microwells per $cm^2$, at least 100,000 microwells per $cm^2$, or at least 160,000 microwells per $cm^2$). A substrate of a microfabricated chip may include about or more than 10,000,000 microwells or locations. For example, an array of microwells may include at least 96 locations, at least 1,000 locations, at least 5,000 locations, at least 10,000 locations, at least 50,000 locations, at least 100,000 locations, at least 500,000 locations, at least 1,000,000 locations, at least 5,000,000 locations, or at least 10,000,000 locations. The arrays of microwells may form grid patterns, and be grouped into separate areas or sections. The dimensions of a microwell may range from nanoscopic (e.g., a diameter from about 1 to about 100 nanometers) to microscopic. For example, each microwell may have a diameter of about 1 μm to about 800 μm, a diameter of about 25 μm to about 500 μm, or a diameter of about 30 μm to about 100 μm. A microwell may have a diameter of about or less than 1 μm, about or less than 5 μm, about or less than 10 μm, about or less than 25 μm, about or less than 50 μm, about or less than 100 μm, about or less than 200 μm, about or less than 300 μm, about or less than 400 μm, about or less than 500 μm, about or less than 600 μm, about or less than 700 μm, or about or less than 800 μm. In exemplary embodiments, the diameter of the microwells can be about 100 μm or smaller, or 50 μm or smaller. A microwell may have a depth of about 25 μm to about 100 μm, e.g., about 1 μm, about 5 μm, about 10 μm, about 25 μm, about 50 μm, about 100 μm. It can also have greater depth, e.g., about 200 μm, about 300 μm, about 400 μm, about 500 μm. The spacing between adjacent microwells can range from about 25 μm to about 500 μm, or about 30 μm to about 100 μm.

Figure 1:
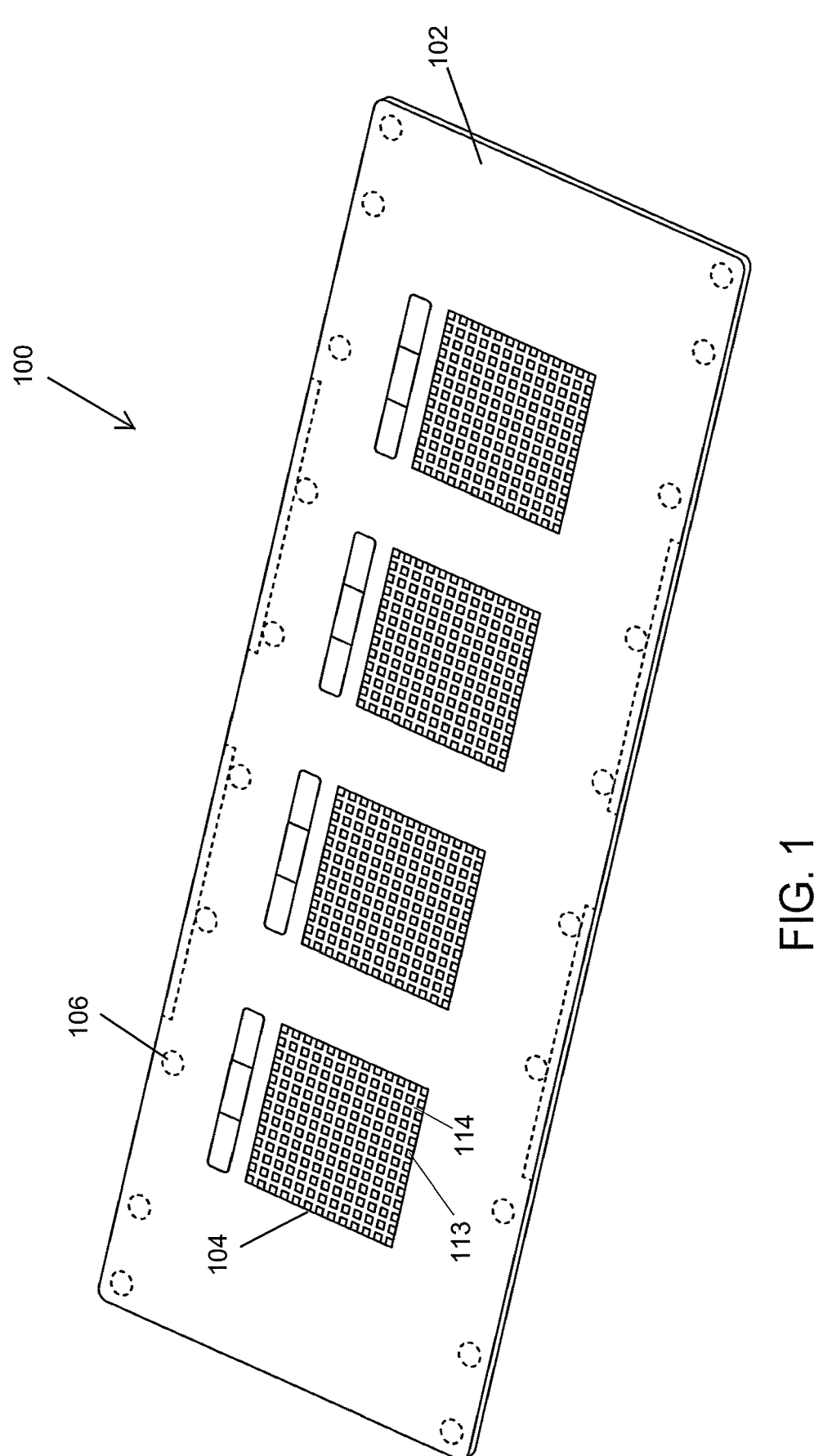
FIG. 1 is a perspective view illustrating a microfabricated device or chip in accordance with some embodiments.

The microfabricated chip can have two major surfaces: a top surface and a bottom surface, where the microwells have openings at the top surface. Each microwell of the microwells may have an opening or cross section having any shape, e.g., round, hexagonal, square, or other shapes. Each microwell may include sidewalls. For microwells that are not round in their openings or cross sections, the diameter of the microwells described herein refer to the effective diameter of a circular shape having an equivalent area. For example, for a square shaped microwell having side lengths of 10×10 microns, a circle having an equivalent area (100 square microns) has a diameter of 11.3 microns. Each microwell may include a sidewall or sidewalls. The sidewalls may have a cross-sectional profile that is straight, oblique, and/or curved. Each microwell includes a bottom which can be flat, round, or of other shapes. The microfabricated chip (with the microwells thereon) may be manufactured from a polymer, e.g., a cyclic olefin polymer, via precision injection molding or some other process such as embossing. Other material of construction is also available, such as silicon and glass. The chip may have a substantially planar major surface. FIG. 1 shows a schematic depiction of a microfabricated chip, whose edges are generally parallel to the directions of the rows and the columns of the microwells on the chip.

The high density microwells on the microfabricated chip can be used for receiving a sample comprising at least one biological entity (e.g., at least one cell). The term "biological entity" may include, but is not limited to, an organism, a cell, a cell component, a cell product, and a virus, and the term "species" may be used to describe a unit of classification, including, but not limited to, an operational taxonomic unit (OTU), a genotype, a phylotype, a phenotype, an ecotype, a history, a behavior or interaction, a product, a variant, and an evolutionarily significant unit. The high density microwells on the microfabricated chip can be used to conduct various experiments, such as growth or cultivation or screening of various species of bacteria and other microorganisms (or microbes) such as aerobic, anaerobic, and/or facultative aerobic microorganisms. The microwells may be used to conduct experiments with eukaryotic cells such as mammalian cells. Also, the microwells can be used to conduct various genomic or proteomic experiments, and may contain cell products or components, or other chemical or biological substances or entities, such as a cell surface (e.g., a cell membrane or wall), a metabolite, a vitamin, a hormone, a neurotransmitter, an antibody, an amino acid, an enzyme, a protein, a saccharide, ATP, a lipid, a nucleoside, a nucleotide, a nucleic acid (e.g., DNA or RNA), a chemical, e.g., a dye, enzyme substrate, etc.

In some embodiments, the high density cell cultivation platform can be droplet based, e.g., instead of array(s) of wells as experimental units on a microfabricated chip, a population of discrete droplets can be used to retain cells, media and other components for cell cultivation. Droplet generation methods, especially when combined with cell-sorter-on-a-chip type instrumentation, may be used to grow and screen microbes from a complex environmental sample. Droplets may be produced at several hundred Hz, meaning millions of drops can be produced in a few hours. A simple chip-based device may be used to generate droplets and the droplets may be engineered to contain a single cell. A system for generating droplets containing cell suspensions may contain one or small numbers of cells. The droplets can be emulsions, double emulsion, hydrogel, bubbles and complex particles, etc. For example, aqueous drops may be suspended in a nonmiscible liquid keeping them apart from each other and from touching or contaminating any surfaces. The volume of a droplet can be somewhere between 10 fl and 1 μL, and highly monodisperse droplets can be made from a few nanometers up to 500 μm in diameter. A droplet-based microfluidic system may be used to generate, manipulate, and/or incubate small droplets. Cell survival and proliferation can be similar to control experiments in bulk solution. Fluorescence screening of droplets may be done on-chip and at a rate of, for example, 500 drops per second. Droplets may be merged to create a new droplet or a reagent added to a droplet. Droplets can be passed in a microchannel in a single file and interrogated by a spectroscopic method, e.g., using a fluorescence detector to detect fluorescence emitted from the droplets, and those droplets that are determined to meet certain criteria (e.g., emitting fluorescence at certain wavelength) can be selected via diversion into a branched channel from which the droplet can be pooled or harvested. The diversion or switching of flow can be accomplished by valves, pump, applying an external electric field, etc.

In various embodiments, a cell may be Archaea, Bacteria, or Eukaryota (e.g., fungi). For example, a cell may be a microorganism, such as an aerobic, anaerobic, or facultative aerobic microorganisms. A virus may be a bacteriophage. Other cell components/products may include, but are not limited to, proteins, amino acids, enzymes, saccharides, adenosine triphosphate (ATP), lipids, nucleic acids (e.g., DNA and RNA), nucleosides, nucleotides, cell membranes/walls, flagella, fimbriae, organelles, metabolites, vitamins, hormones, neurotransmitters, and antibodies.

For the cultivation of cells, a nutrient is often provided. A nutrient may be defined (e.g., a chemically defined or synthetic medium) or undefined (e.g., a basal or complex medium). A nutrient may include or be a component of a laboratory-formulated and/or a commercially manufactured medium (e.g., a mix of two or more chemicals). A nutrient may include or be a component of a liquid nutrient medium (i.e., a nutrient broth), such as a marine broth, a lysogeny broth (e.g., Luria broth), etc. A nutrient may include or be a component of a liquid medium mixed with agar to form a solid medium and/or a commercially available manufactured agar plate, such as blood agar.

A nutrient may include or be a component of selective media. For example, selective media may be used for the growth of only certain biological entities or only biological entities with certain properties (e.g., antibiotic resistance or synthesis of a certain metabolite). A nutrient may include or be a component of differential media to distinguish one type of biological entity from another type of biological entity or other types of biological entities by using biochemical characteristics in the presence of specific indicator (e.g., neutral red, phenol red, eosin y, or methylene blue).

A nutrient may include or be a component of an extract of or media derived from a natural environment. For example, a nutrient may be derived from an environment natural to a particular type of biological entity, a different environment, or a plurality of environments. The environment may include, but is not limited to, one or more of a biological tissue (e.g., connective, muscle, nervous, epithelial, plant epidermis, vascular, ground, etc.), a biological fluid or other biological product (e.g., amniotic fluid, bile, blood, cerebrospinal fluid, cerumen, exudate, fecal matter, gastric fluid, interstitial fluid, intracellular fluid, lymphatic fluid, milk, mucus, rumen content, saliva, sebum, semen, sweat, urine, vaginal secretion, vomit, etc.), a microbial suspension, air (including, e.g., different gas contents), supercritical carbon dioxide, soil (including, e.g., minerals, organic matter, gases, liquids, organisms, etc.), sediment (e.g., agricultural, marine, etc.), living organic matter (e.g., plants, insects, other small organisms and microorganisms), dead organic matter, forage (e.g., grasses, legumes, silage, crop residue, etc.), a mineral, oil or oil products (e.g., animal, vegetable, petrochemical), water (e.g., naturally-sourced freshwater, drinking water, seawater, etc.), and/or sewage (e.g., sanitary, commercial, industrial, and/or agricultural wastewater and surface runoff).

FIG. 1 is a perspective view illustrating a microfabricated device or chip in accordance with some embodiments. Chip 100 includes a substrate shaped in a microscope slide format with injection-molded features on top surface 102. The features include four separate microwell arrays (or microarrays) 104 as well as ejector marks 106. The microwells 113 (spaced by interstitial space 114) in each microarray are arranged in a grid pattern with well-free margins around the edges of chip 100 and between microarrays 104.

Figures 2A, 2B, 2C:
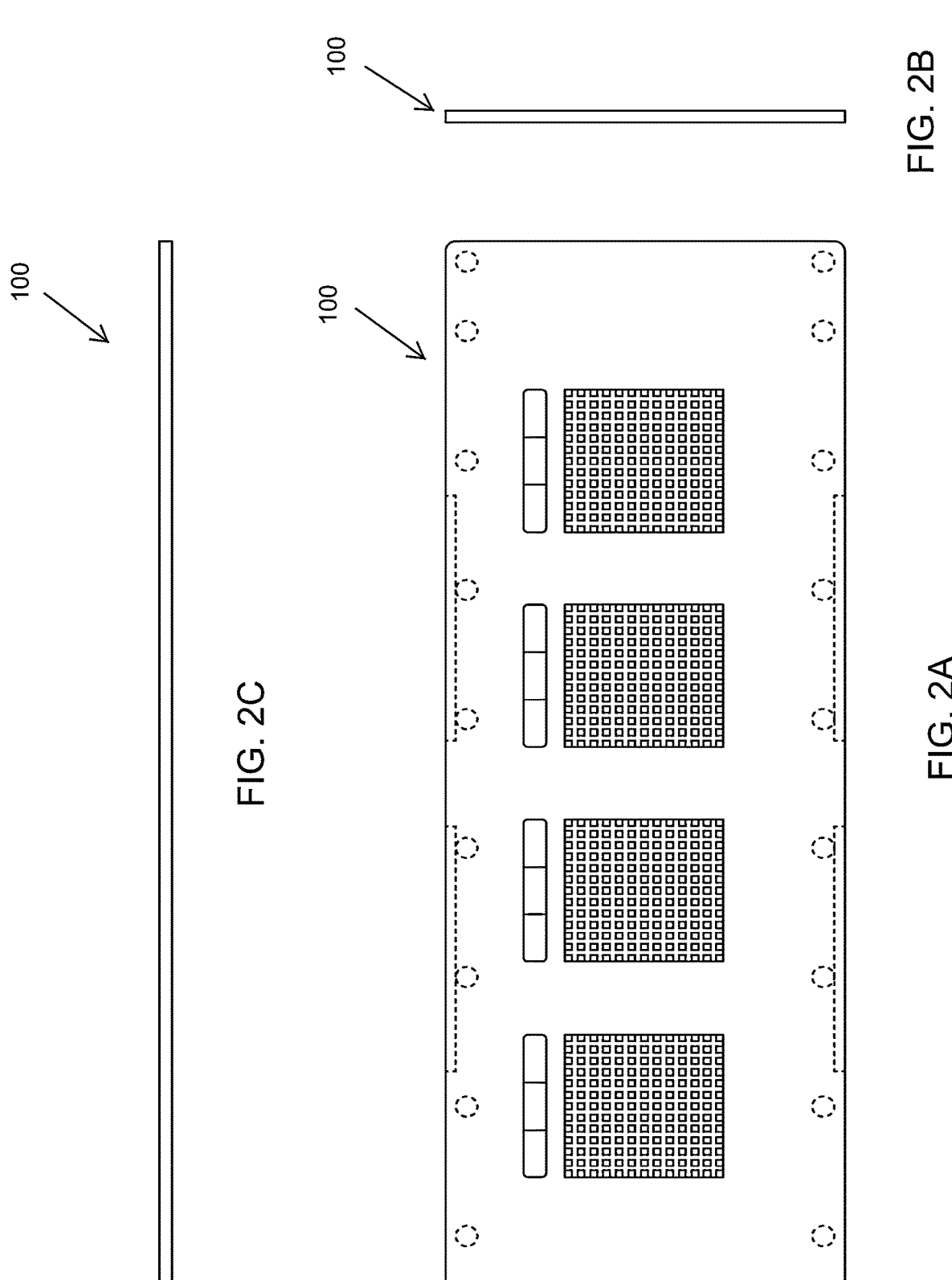
FIGS. 2A-2C are top, side, and end views, respectively, illustrating dimensions of microfabricated device or chip in accordance with some embodiments.

FIGS. 2A-2C are top, side, and end views, respectively, illustrating dimensions of chip 100 in accordance with some embodiments. In FIG. 2A, the top of chip 100 is approximately 25.5 mm by 75.5 mm. In FIG. 2B, the end of chip 100 is approximately 25.5 mm by 0.8 mm. In FIG. 2C, the side of chip 100 is approximately 75.5 mm by 0.8 mm.

Figure 3A:
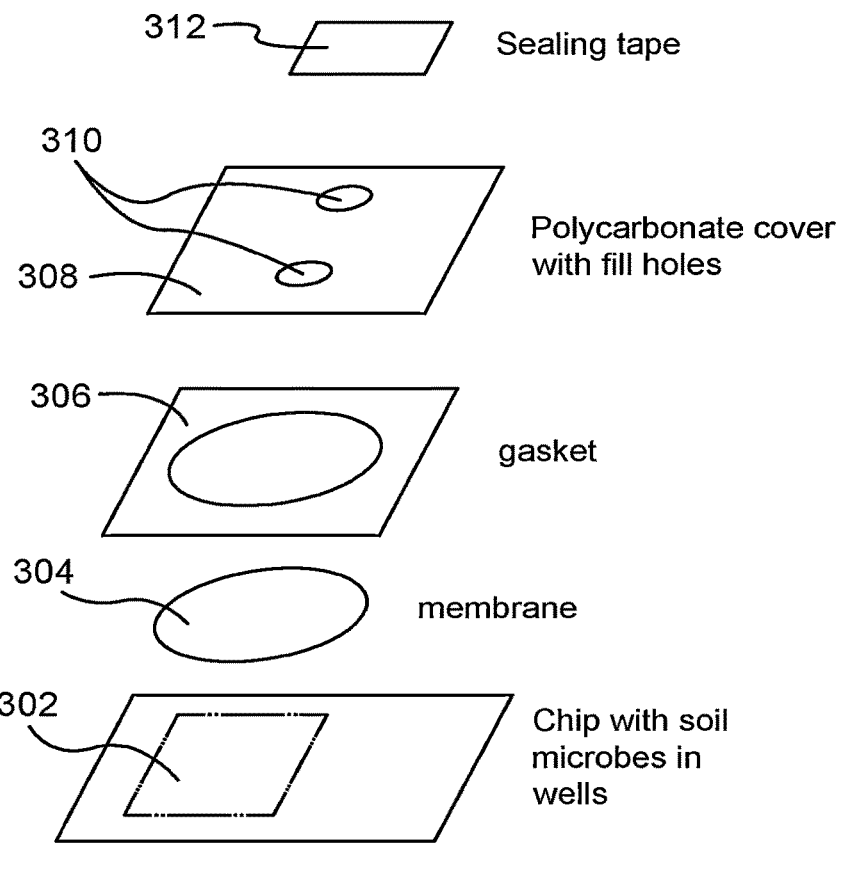
FIGS. 3A and 3B are exploded and top views, respectively, illustrating a microfabricated device or chip in accordance with some embodiments.
Figure 3B:
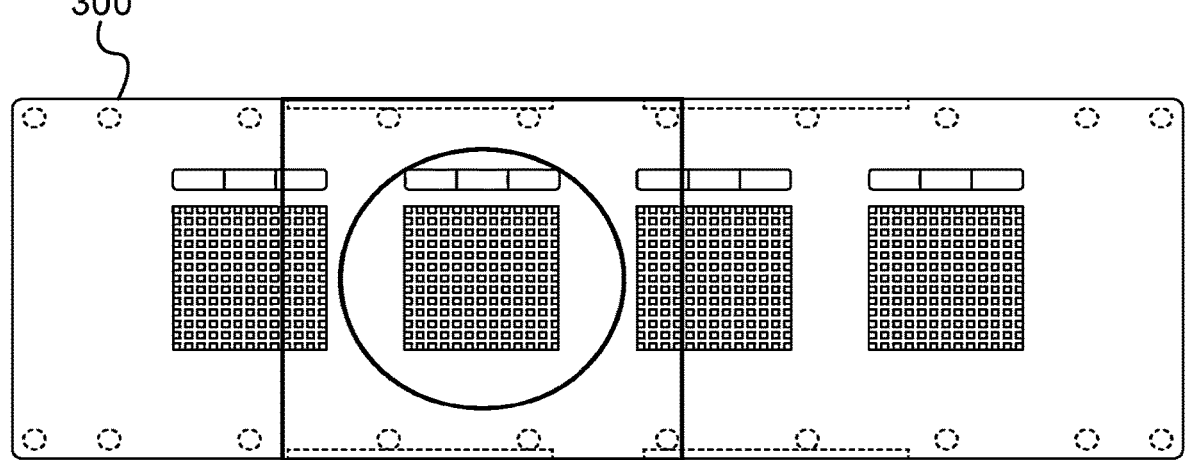

After a sample is loaded on a microfabricated device, a membrane may be applied to at least a portion of a microfabricated device. FIG. 3A is an exploded diagram of the microfabricated device 300 shown from a top view in FIG. 3B in accordance with some embodiments. Device 300 includes a chip with an array of wells 302 holding, for example, soil microbes or human microbiome. A membrane 304 is placed on top of the array of wells 302. A gasket 306 is placed on top of the membrane 304. A cover 308 with fill holes 310 is placed on top of the gasket 306. Finally, sealing tape 312 is applied to the cover 308.

A membrane may cover at least a portion of a microfabricated device including one or more experimental units or microwells. For example, after a sample is loaded on a microfabricated device, at least one membrane may be applied to at least one microwell of a high density array of microwells. A plurality of membranes may be applied to a plurality of portions of a microfabricated device. For example, separate membranes may be applied to separate subsections of a high density array of microwells.

A membrane may be connected, attached, partially attached, affixed, sealed, and/or partially sealed to a microfabricated device to retain at least one biological entity in the at least one microwell of the high density array of microwells. For example, a membrane may be reversibly affixed to a microfabricated device using lamination. A membrane may be punctured, peeled back, detached, partially detached, removed, and/or partially removed to access at least one biological entity in the at least one microwell of the high density array of microwells.

A portion of the population of cells in at least one experimental unit, well, or microwell may attach to a membrane (via, e.g., adsorption). If so, the population of cells in at least one experimental unit, well, or microwell may be sampled by peeling back the membrane such that the portion of the population of cells in the at least one experimental unit, well, or microwell remains attached to the membrane.

A membrane may be impermeable, semi-permeable, selectively permeable, differentially permeable, and/or partially permeable to allow diffusion of at least one nutrient into the at least one microwell of a high density array of microwells. For example, a membrane may include a natural material and/or a synthetic material. A membrane may include a hydrogel layer and/or filter paper. In some embodiments, a membrane is selected with a pore size small enough to retain at least some or all of the cells in a microwell. For mammalian cells, the pore size may be a few microns and still retain the cells. However, in some embodiments, the pore size may be less than or equal to about 0.2 μm, such as 0.1 μm. An impermeable membrane has a pore size approaching zero. It is understood that the membrane may have a complex structure that may or may not have defined pore sizes.

In one aspect, a method of identifying a fluorescent cell in a sample using a microfabricated chip having a top surface including a plurality of microwells, is provided. The method includes: (a) loading at least one cell of a sample into at least one microwell of the plurality of microwells; (b) incubating the microfabricated chip (at suitable temperature and for suitable duration of time, as appropriate for the cell types and growth conditions, etc.) to grow a population of cells from the at least one cell in the at least one microwell; and (c) detecting fluorescence exhibited by at least one microwell by analyzing an image of the microfabricated chip, to thereby determine a presence of a fluorescent cell of interest in the sample.

In some embodiments, the loading comprises loading a plurality of cells of the sample into the plurality of microwells such that at least some of the plurality of microwells each contain one cell, and none or only statistically insignificant percentage of the plurality of microwells contains more than one cell. By "statistically insignificant", it is meant that the chance of any microwells contain more than one cell is less than 0.1 percent, preferably less than 0.01 percent, and more preferably 0.001 percent. In this manner, it can be ensured that the population of cells grown in a single microwell is of a single strain or species, making it easier for downstream pure isolate recovery and analysis.

In some embodiments, the at least one microwell of the plurality of microwells is also loaded with a metabolic indicator which indicates metabolic activity of cells, such as resazurin. The loading can be performed prior to, together with, or after the loading of the cells. The metabolic indicator can have fluorescent properties that can be affected by the metabolic activity of cells, such as cell growth and proliferation. For example, resazurin, a commonly used fluorescent dye, can be used. The fluorescence of resazurin can be reduced in an environment of viable cell growth and change from blue/purple to pink.

In some embodiments, detecting the fluorescence of the microwell comprises detecting fluorescence of the metabolic indicator and fluorescence of the population of cells at separate fluorescence detection channels. The detection can be conducted simultaneously in different channels.

Herein, the detected fluorescence of the population of cells reflects an innate fluorescence of the fluorescent cell of interest (a naturally occurring fluorescent cell, or a genetically-modified cell that has fluorescent properties), which enhances naturally when a cell if a microwell grows and multiplies. In some embodiments, if a fluorescence of the population of cells contained in a microwell is detected, at least one cell from the population of cells in the at least one microwell can be transferred to a target location, e.g., a 96-well plate containing growth media, for further cultivation, growth, analysis, etc.

In some embodiments, after the loading and before the incubation, a membrane is applied to retain the one cell in the at least one microwell.

The at least one cell can include a cell, a bacteria cell, an Archaea cell, or a eukaryotic cell.

In an example, the screening methods herein utilize Applicant's Prospector system which is a high-throughput isolation, cultivation and screening system that uses a microfabricated chip described herein for cultivation of 100s to 1000s of microbes from complex samples in parallel in separate microwells using an automated workflow. The system has integrated onboard optics that can emit excitation wavelengths and capture fluorescent images in the red (635 nm), green (532 nm) and blue channels (488 nm). The optics could be used to detect bacteria that are expressing GFP which exhibits fluorescence when exposed to light in the blue to ultraviolet range.

Example 1

A mixed community of *E. coli* ATCC 25922 and *E. coli* ATCC 25922GFP (American Type Culture Collection, Manassas, Virginia, USA) was created. ATCC 25922GFP was derived from ATCC 25922 and contains a multicopy vector encoding GFPmut3 expressed under the control of the $P_{lac}$ promoter, a construct designed for fluorescence labeling of Gram-negative bacteria.

Liquid cultures of the two *E. coli* strains were grown individually overnight in LB bacteria growth medium at room temperature. The cultures were then combined 50/50, diluted 1:100,000 in LB medium, spiked with resazurin indicator to a final concentration of 100 μM, and loaded on the 6109 microwells of a microfabricated chip such that on average each microwell is loaded with less than 0.4 cells. The dilution factor and the microwell loading techniques can be adjusted to ensure that at least some microwells are each loaded with one and only one cell and no microwells are loaded with more than one cell (or it is extremely unlikely any microwells are loaded with more than one cell). The microfabricated chip was incubated at room temperature for 24 hours. Approximately 1600 positives were detected by the change of color of resazurin on the microfabricated device used in the following analysis, meaning that microbial growth was detected in over one-fourth of the 6109 microwells of the microfabricated chip.

The microfabricated chip was imaged under each fluorescence channel after 24 hours of incubation at room temperature, and a scatter plot (FIG. 4) comparing blue and red fluorescence was generated. Each point of the scatter plot represents a microwell on the microfabricated chip. All microwells containing microbial growth are low in red fluorescence, as the resazurin detected in the red channel has been metabolically driven to resorufin which fluoresces in the green channel. Only the microwells that contain GFP *E. coli* would be high in blue fluorescence. Two distinct clouds of microbial growth are apparent on the scatter plot (FIG. 4), a low-red/high-blue cloud of putative GFP *E. coli* and low-red/low-blue cloud of putative wild type *E. coli*. The high-red/low-blue cloud (round dots) indicates microwells with no microbial growth.

Figure 4:
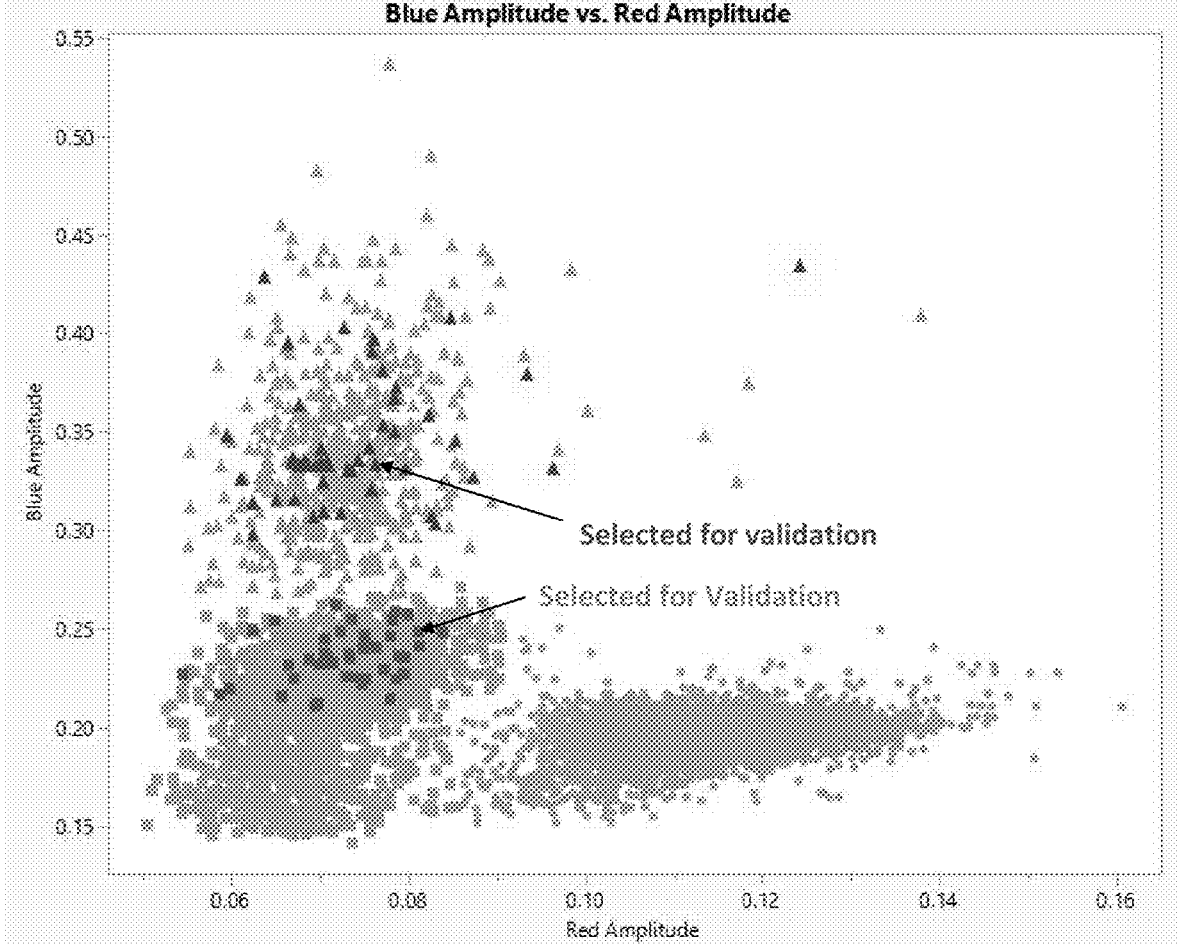
FIG. 4 is a scatter plot showing separation of putative GFP (low-red/high-blue cloud, blue dots (triangle symbols) and putative non-GFP (low-red/low-blue cloud, green dots (square symbols) E. coli according to some embodiments.

A selection of microwells were transferred to an LB-containing 96-well plate to validate that the blue and green clouds of positives detected by Prospector's optics indeed represented GFP-expressing and wild type *E. coli*, respectively. A total of 48 microwells indicating microbial growth with GFP expression were chosen at random from the cloud of low-red/high-blue fluorescent wells (FIG. 4, blue dots), and 44 microwells indicating wild type microbial growth, i.e., no GFP expression, were chosen at random from the cloud of low-red/low-blue fluorescent wells (FIG. 4, green dots). Four wells of the 96 well plate were reserved as negative controls containing LB only.

The 96-well transfer plate was measured on a fluorescence plate reader at 526 nm with 488 nm excitation after 24 hours of incubation at 30° C. The fold change in fluorescence was compared between wild type and GFP-expressing *E. coli*, relative to the average of the four negative control wells (Table 1). The results indicate 100% accuracy in selection of the GFP vs non-GFP wells for transfer, and that each time what was retrieved was the intended target.

TABLE 1

| Fold change in GFP fluorescence at 526 nm following overnight incubation in 96-well plate | | |
|---|---|---|
| Fold change parameter | GFP *E. coli* | wild type *E. coli* |
| mean | 26.2 | 1.32 |
| median | 28.5 | 1.29 |
| maximum | 47.0 | 1.6 |
| minimum | 2.4 | 1.1 |
| coefficient of variation % | 38.52% | 11.43% |

Figure 5:
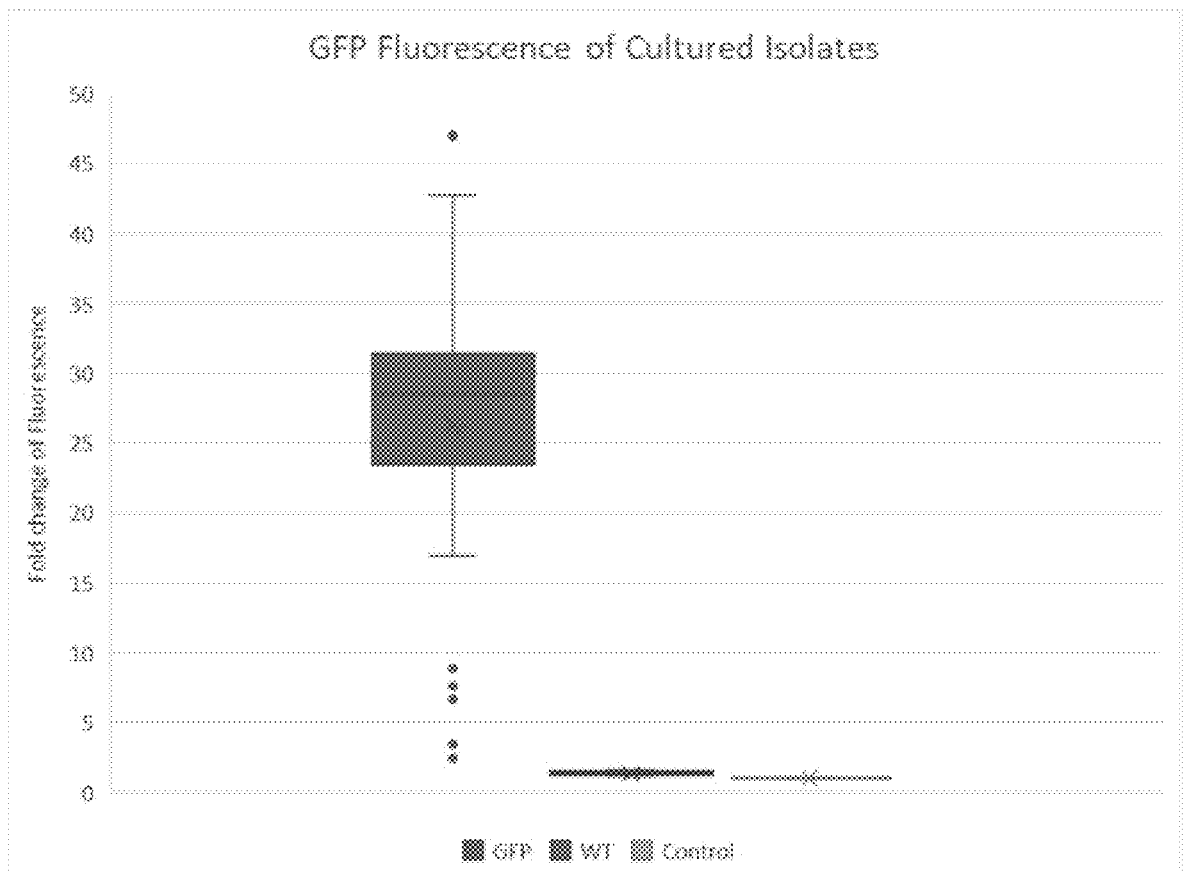
FIG. 5 is a box-and-whisker plot of fluorescence fold-change variability in GFP- vs non-GFP-expressing transfers to 96-well plate according to some embodiments.

The wider range in fold change across the wells containing GFP *E. coli* seen in Table 1 and displayed graphically in the box-and-whisker plot (FIG. 5) is likely due to the natural variability in GFP expression. This measurement shows that the Prospector's imaging system can clearly differentiate GFP-tagged bacteria from wild type bacteria on the microfabricated chip and the successful transfer of those isolates to a 96 well plate. These results demonstrate the capability of the disclosed methods to screen for GFP-expressing bacteria in viable cultures.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of identifying a fluorescent live cell using a microfabricated chip having a top surface including a plurality of microwells, the method comprising:
   (a) loading at least one cell of a sample into at least one microwell of the plurality of microwells, wherein the at least one microwell is also loaded with a metabolic indicator which is a fluorescent dye indicating the metabolic activity of cells;
   (b) incubating the microfabricated chip to grow a population of cells from the at least one cell in the at least one microwell; and
   (c) detecting fluorescence exhibited by at least one microwell by analyzing an image of the microfabricated chip, to thereby determine a presence of a fluorescent live cell of interest in the sample,
   wherein the detecting comprises detecting fluorescence of the metabolic indicator and fluorescence of the population of cells simultaneously at separate fluorescence detection channels.

2. The method of claim 1, wherein the loading comprises loading a plurality of cells of the sample into the plurality of microwells such that at least some of the plurality of microwells each contain one and only one cell, while statistically insignificant percentage of the plurality of microwells contains more than one cell.

3. The method of claim 1, further comprising:
   if fluorescence of the population of cells is detected, transferring at least one cell from the population of cells in the at least one microwell to a target location.

4. The method of claim 1, further comprising applying a membrane to retain the at least one cell in the at least one microwell.

5. The method of claim 1, wherein the at least one cell includes at least one of a cell, a bacteria cell, an Archaea cell, and a eukaryota cell.

6. A method of identifying a fluorescent live cell in a sample using a microfabricated chip having a top surface including a plurality of microwells, the method comprising:
   (a) loading at least one cell of a sample and a fluorescent metabolic indicator being a fluorescent dye into at least one microwell of the plurality of microwells, the fluorescence status of the metabolic indicator indicating presence or absence of cell metabolic activity;
   (b) incubating the microfabricated chip to grow a population of cells from the at least one cell in the at least one microwell;
   (c) detecting fluorescence exhibited by at least one microwell by analyzing an image of the microfabricated chip, to thereby determine a presence of a fluorescent live cell of interest in the sample,
   wherein detecting fluorescence exhibited by at least one microwell comprises detecting fluorescence of the metabolic indicator and fluorescence of the population of cells simultaneously at separate fluorescence detection channels.

* * * * *